United States Patent
Hashimoto et al.

(10) Patent No.: US 6,333,431 B1
(45) Date of Patent: Dec. 25, 2001

(54) PROCESSES FOR THE PREPARATION OF FLUORINATED BENZOIC ACIDS

(75) Inventors: Akihiro Hashimoto, Tokushima; Satoshi Matsuda, Naruto; Kuninori Tai, Tokushima; Hitoshi Tone, Tokushima; Takao Nishi, Tokushima; Jun-ichi Minamikawa, Naruto; Michiaki Tominaga, Tokushima, all of (JP)

(73) Assignee: Otsuka Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 09/786,522

(22) PCT Filed: Sep. 9, 1999

(86) PCT No.: PCT/JP99/04923

§ 371 Date: Mar. 6, 2001

§ 102(e) Date: Mar. 6, 2001

(87) PCT Pub. No.: WO00/15596

PCT Pub. Date: Mar. 23, 2000

(30) Foreign Application Priority Data

Sep. 14, 1998 (JP) .................................................. 10-259957

(51) Int. Cl.$^7$ .................................................. C07C 63/04
(52) U.S. Cl. ............................................................. 562/493
(58) Field of Search .............................................. 562/493

(56) References Cited

U.S. PATENT DOCUMENTS

| | | | |
|---|---|---|---|
| 4,920,120 | * | 4/1990 | Domagala et al. . |
| 5,290,934 | * | 3/1994 | Ueda et al. . |
| 5,585,491 | * | 12/1996 | Domagala et al. . |
| 5,811,576 | * | 9/1998 | Ueda et al. . |

FOREIGN PATENT DOCUMENTS

19850788 * 5/2000 (EP) .

OTHER PUBLICATIONS

Hagen et al, Synthesis of 5-methyl-4- oxo-quinolinecarboxylic acids, J. Heterocyclic Chem. 27, 1609, 1990.*

Hagen et al, Synthesis and BiologicalActivity of 5-Alkyl-1,7,8-trisubstituted -6-fluoroquinoline-3-carboxylic acids, J. Med. Chem., 34, 1155-1161, 1991.*

* cited by examiner

Primary Examiner—Gary Geist
Assistant Examiner—Hector M Reyes
(74) Attorney, Agent, or Firm—Finnegan, Henderson, Farabow, Garrett & Dunner LLP

(57) ABSTRACT

An object of the present invention is to provide a commercially advantageous process for preparing a fluoro benzoic acid. The process according to the present invention comprises either alkylating a fluoro benzoic acid of the formula

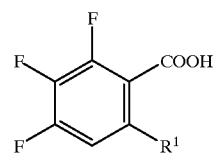

(3)

wherein $R^1$ is halogen, or reducing a fluoro benzoic acid of the formula

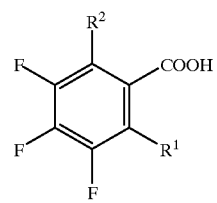

(4)

wherein $R^1$ is as defined above and $R^2$ is lower alkyl to thereby produce a fluoro benzoic acid represented by the formula

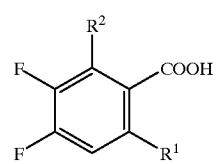

(2)

wherein $R^1$ and $R^2$ are as defined above.

18 Claims, No Drawings

PROCESSES FOR THE PREPARATION OF FLUORINATED BENZOIC ACIDS

TECHNICAL FIELD

The present invention relates to a process for preparing a fluoro benzoic acid.

BACKGROUND ART

Benzo heterocyclic derivatives represented by the formula (1) shown below have excellent antibacterial activity and are useful as antibacterial agents (Japanese Examined Patent Publication No. 96557/1994).

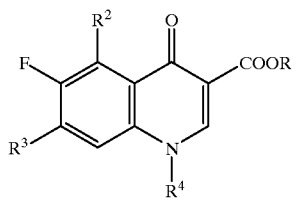
(1)

In the formula, $R^2$ is $C_{1-6}$ alkyl. $R^3$ is a 5- to 9-membered saturated or unsaturated heterocyclic ring residue, the heterocyclic ring residue optionally having one or more substituents. $R^4$ is cyclopropyl which may be substituted by 1 to 3 substituents selected from the group consisting of $C_{1-6}$ alkyl and halogen; phenyl which may be substituted by 1 to 3 substituents selected from the group consisting of $C_{1-6}$ alkoxy, halogen and hydroxy on the phenyl ring; $C_{1-6}$ alkyl which may be substituted by halogen, $C_{2-6}$ alkanoyloxy or hydroxy; $C_{2-6}$ alkenyl or thienyl. R is hydrogen or $C_{1-6}$ alkyl.

More specifically, the benzo heterocyclic derivatives of the formula (1) and salts thereof have excellent antibacterial activities against various gram-positive bacteria and gram-negative bacteria and are useful for the treatment of various infectious diseases induced by various bacteria in human, other animals and fish and also useful as an external antimicrobial or disinfectant agent for medical instruments and the like. The benzo heterocyclic derivatives of the formula (1) and salts thereof show an excellent antibacterial activity against mycoplasma, *Pseudomonas aeruginosa*, anaerobic bacteria, resistant cells against various antibacterials, clinically isolated strains, and gram negative and gram positive bacteria such as *Enterococcus faecalis* and *Staphyloccocus pyognes* and hence are useful as an antibacterial agent for the treatment of diseases induced by these microorganisms. The benzo heterocyclic derivatives of the formula (1) and salts thereof show low toxicity and less side effect and have characteristic features such as good absorbability and sustained activity. Furthermore, the benzo heterocyclic derivatives of the formula (1) and salts thereof are useful for the treatment of urinary infectious diseases because they are highly excreted via urine, and further because of easy excretion via bile, they are useful for the treatment of intestinal infectious diseases.

According to Japanese Examined Patent Publication No. 96557/1994, the benzo heterocyclic derivatives of the formula (1) and salts thereof are prepared by using a fluoro benzoic acid of the formula (2)

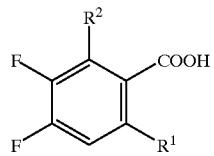
(2)

wherein $R^2$ is as defined above and $R^1$ is halogen.

According to Japanese Examined Patent Publication No. 96557/1994, as shown below in Reaction Scheme A or B, a fluoro benzoic acid of the formula (2) is prepared by using known starting compounds by a multiple-step process comprising five steps. Thus according to the process described in Japanese Examined Patent Publication No. 96557/1994, a complicated reaction procedure must be carried out to prepare the fluoro benzoic acid of the formula (2). Furthermore, the desired fluoro benzoic acid of the formula (2) is obtained only in a low yield of about 8.3%.

Reaction Scheme A

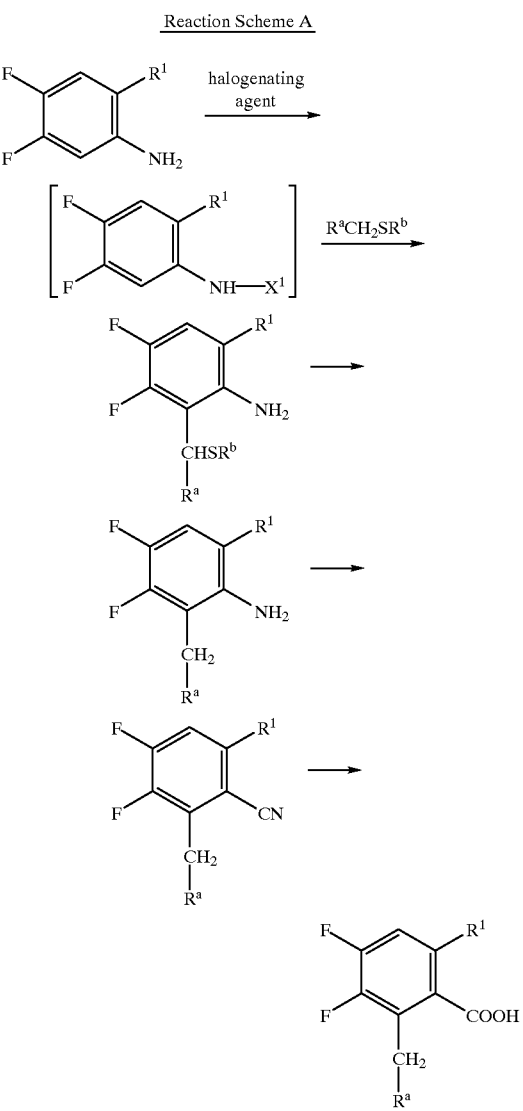

wherein $R^1$ is as defined above, $R^a$ is hydrogen or $C_{1-6}$ alkyl, $R^b$ is $C_{1-6}$ alkyl, and $X^1$ is halogen.

Reaction Scheme B

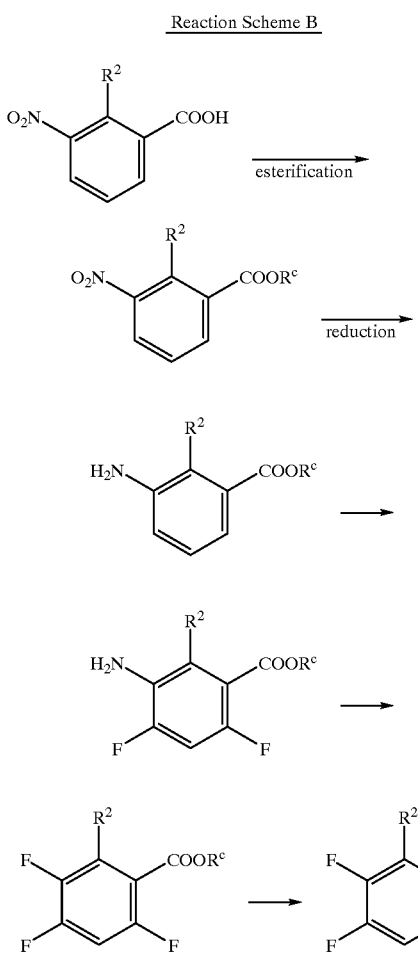

wherein $R^2$ is as defined above and $R^c$ is $C_{1-6}$ alkyl.

Japanese Unexamined Patent Publications Nos. 243692/1990 and 74167/1992 and EP319906 disclose a process for preparing a fluoro benzoic acid of the formula (2) by using a compound of the formula (A), as shown in the following Reaction Scheme C:

Reaction Scheme C

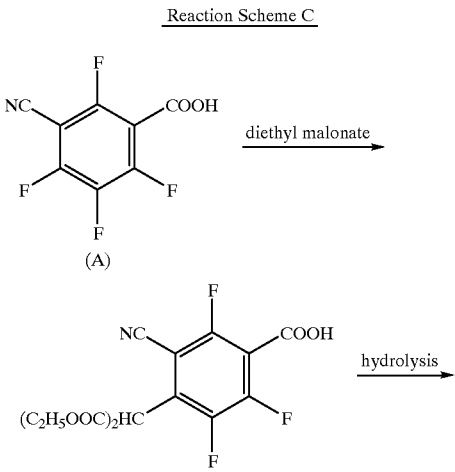

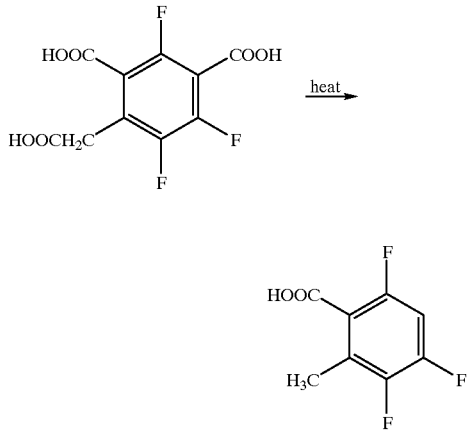

The process, however, necessitates undertaking three steps to prepare the desired fluoro benzoic acid by using the compound of the formula (A). Furthermore, the desired fluoro benzoic acid is obtained only in a low yield of about 7.5%, based on the compound of the formula (A).

Japanese Unexamined Patent Publications Nos. 502452/1991 and 291959/1998 and J. Heterocyclic Chem., 27, p1610 (1990) disclose a process for preparing a fluoro benzoic acid of the formula (2) by using a compound of the formula (B), as shown in the following Reaction Scheme D:

Reaction Scheme D

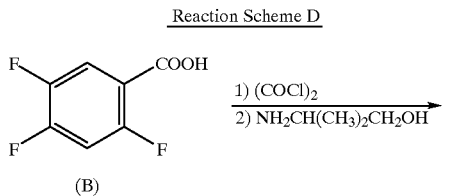

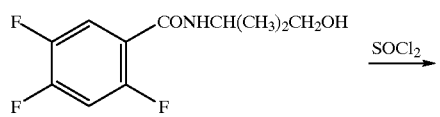

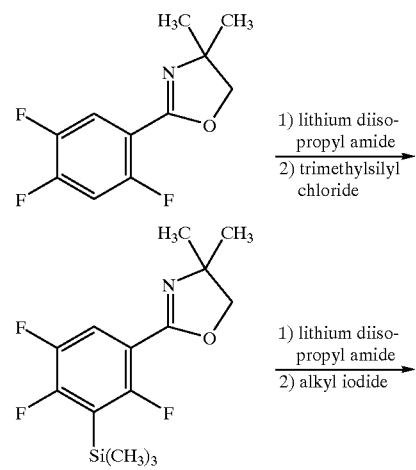

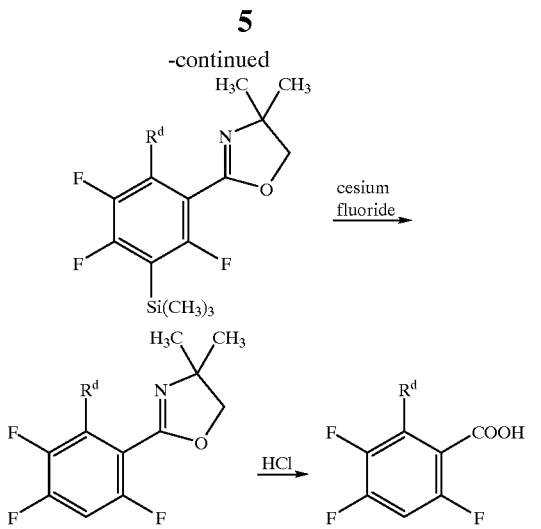

wherein $R^d$ is alkyl.

The process, however, necessitates undertaking seven steps to prepare the desired fluoro benzoic acid by using the compound of the formula (B). Furthermore, the desired fluoro benzoic acid is obtained only in a low yield of about 45.8%, based on the compound of the formula (B).

J. Heterocyclic Chem., 27, p.1611 (1990) and Journal of Medicinal Chemistry, 1991, vol.34, No.3, p.1156 disclose a process for preparing a fluoro benzoic acid of the formula (2) by using the compound of the formula (C), as shown in the following Reaction Scheme E:

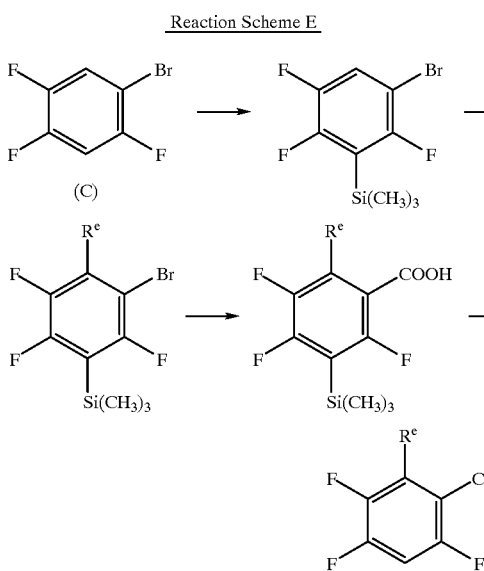

wherein $R^e$ is methyl or ethyl.

The process, however, necessitates undertaking four steps to prepare the desired fluoro benzoic acid by using the compound of the formula (C). Furthermore, the desired fluoro benzoic acid is obtained only in a low yield of about 25 to 30%, based on the compound of the formula (C).

DISCLOSURE OF THE INVENTION

An object of the present invention is to provide a single step process for preparing a fluoro benzoic acid of the formula (2) without the necessity of undertaking multiple steps, the fluoro benzoic acid being used as an intermediate for preparing a benzo heterocyclic derivative of the formula (1) which is useful as an antibacterial agent.

Another object of the present invention is to provide a process for preparing the fluoro benzoic acid of the formula (2) by a simple and convenient procedure at low costs, using an easily available compound without using any special reagents.

A further object of the present invention is to provide a process for preparing the fluoro benzoic acid of the formula (2) in high purity and high yield.

A still further object of the present invention is to provide a commercially advantageous process for preparing the fluoro benzoic acid of the formula (2).

In view of such state, the inventors of the present invention carried out extensive research to achieve the above objects. During the research, the present inventors conceived of using as a starting material a fluoro benzoic acid of the formula (3)

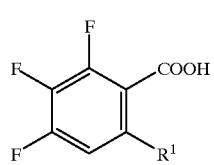

wherein $R^1$ is as defined above. The fluoro benzoic acid of the formula (3) is a compound which is unsubstituted at the 5-position with respect to the carboxyl group.

Izv. Sib. Otd. Akad. Nauk SSSR, Ser. Khim. Nauk, Vol.5, p100 (1975) discloses a process for preparing a compound of the formula (F) comprising reacting a compound of the formula (D) with a Grignard reagent (E), as shown in the following Reaction Scheme F:

Reaction Scheme F

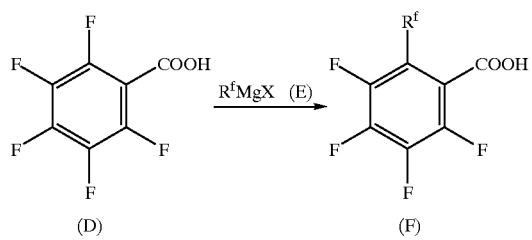

The process produces the compound of the formula (F) in a high yield, but it is presumably owing to the chemical structure of the compound of the formula (D) used as a starting material. Stated more specifically, the compound of the formula (D) is a compound wherein all the hydrogen atoms on the benzene ring have been replaced by substituents (fluorine atoms and a carboxyl group). Upon substitution reaction with the Grignard reagent (E), a fluorine atom at one of the ortho-positions with respect to the carboxyl group (i.e., at 2- or 6-position) is substituted by $R^f$. Whether $R^f$ replaces either one of the fluorine atoms at the 2- and 6-positions with respect to the carboxyl group, the resulting compound will be a compound represented by the formula (F).

Japanese Examined Patent Publications Nos. 502452/1991 and 291959/1998 disclose a process for preparing a compound of the formula (H), which comprises reacting a compound of the formula (G) with alkyllithium, as shown in the following Reaction Scheme G:

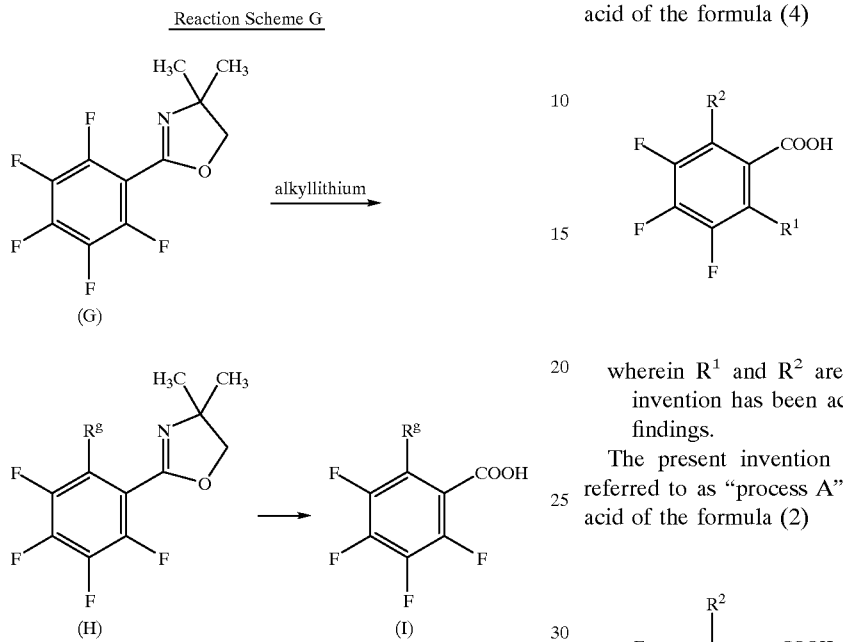

The process produces the compound of the formula (H) in a high yield, but it is presumably owing to the chemical structure of the compound of the formula (G) used as a starting material. Stated more specifically, the compound of the formula (G) is a compound wherein all the hydrogen atoms on the benzene ring have been replaced by substituents (fluorine atoms and a 2-oxazolyl group). Upon substitution reaction with alkyllithium, a fluorine atom at one of the ortho-positions with respect to the 2-oxazolyl group (i.e., 2- or 6-position) is substituted by $R^g$. Whether $R^g$ replaces either one of the fluorine atoms at the 2- and 6-positions with respect to the 2-oxazolyl group, the resulting compound will be a compound represented by the formula (H).

From the conventional reactions as described above, it could easily be assumed that when a fluoro benzoic acid of the formula (3), which is unsubstituted at the 5-position with respect to the carboxyl group, is alkylated with a Grignard reagent (E) or alkyllithium, the resulting compound would have an alkyl group either at the 2-position or at the 6-position with respect to the carboxyl group. Stated more specifically, it had been considered that the reaction would produce two kinds of compounds, i.e., a compound having an alkyl group at the 2-position, and a compound having an alkyl group at the 6-position, the 2- and 6-positions being ortho positions with respect to the carboxyl group of the fluoro benzoic acid of the formula (3). Surprisingly, however, the reaction produces only a trace or no amount of the compound having an alkyl group at the 6-position, which is one of the ortho positions with respect to the carboxyl group of the fluoro benzoic acid of the formula (3), and selectively produces only the compound having an alkyl group at the 2-position, which is the other ortho position with respect to the carboxyl group of the fluoro benzoic acid of the formula (3). Such finding was surprising and unpredictable even to those skilled in the art having chemical knowledge in the field.

The present inventors further found that the object of the invention can also be achieved by reducing a fluoro benzoic acid of the formula (4)

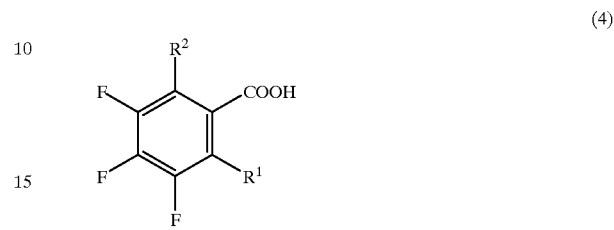

wherein $R^1$ and $R^2$ are as defined above. The present invention has been accomplished based on the above findings.

The present invention provides a process (hereinafter referred to as "process A") for preparing a fluoro benzoic acid of the formula (2)

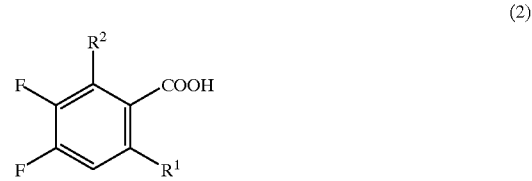

wherein $R^1$ and $R^2$ are as defined above, which comprises alkylating a fluoro benzoic acid of the formula (3)

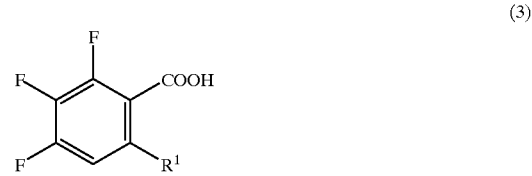

wherein $R^1$ is as defined above.

The present invention further provides a process (hereinafter referred to as "process B") for preparing the fluoro benzoic acid of the formula (2)

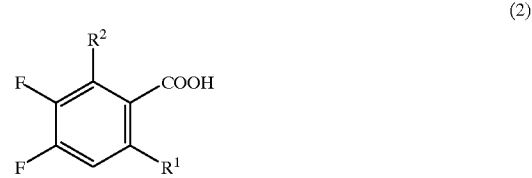

wherein $R^1$ and $R^2$ are as defined above, which comprises reducing a fluoro benzoic acid of the formula (4)

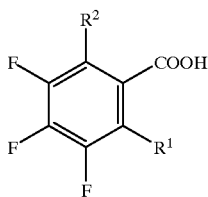

(4)

wherein R¹ and R² are as defined above.

In the specification, $C_{1-6}$ alkyl represented by R² includes $C_{1-6}$ straight chain or branched chain alkyl, such as methyl, ethyl, n-propyl, isopropyl, n-butyl, tert-butyl, n-pentyl, n-hexyl and the like. Particularly preferred $C_{1-6}$ alkyl represented by R² is methyl.

The halogen represented by R¹ includes fluorine, chlorine, bromine and iodine. Particularly preferred halogen is fluorine or bromine.

First, process A is described.

Reaction Scheme-1 (Process A)

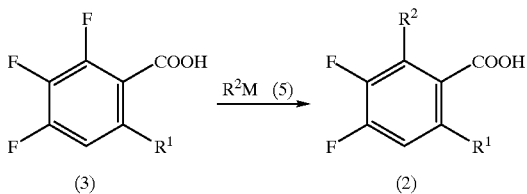

wherein R¹ and R² are as defined above and M is a group of the formula: —MgX (wherein X is halogen), lithium metal or a group of the formula: ZnX (wherein X is as defined above).

In Reaction Scheme-1, the starting compound of the formula (3) and the alkylating agent of the formula (5) are both known compounds that are easily available.

The compound of the formula (3) includes 2,3,4,6-tetrafluorobenzoic acid, 2,3,4-trifluoro-6-chlorobenzoic acid, 2,3,4-trifluoro-6-bromobenzoic acid and the like. Preferred compounds of the formula (3) are 2,3,4,6-tetrafluorobenzoic acid, 2,3,4-trifluoro-6-bromobenzoic acid and the like.

The alkylating agent of the formula (5) includes Grignard reagents such as methyl magnesium bromide, methyl magnesium chloride, methyl magnesium iodide, ethyl magnesium bromide, ethyl magnesium chloride, ethyl magnesium iodide, n-propyl magnesium bromide, n-propyl magnesium chloride, n-propyl magnesium iodide, isopropyl magnesium bromide, isopropyl magnesium chloride, isopropyl magnesium iodide, n-butyl magnesium bromide, n-butyl magnesium chloride, n-butyl magnesium iodide, tert-butyl magnesium bromide, tert-butyl magnesium chloride, tert-butyl magnesium iodide, n-pentyl magnesium bromide, n-pentyl magnesium chloride, n-pentyl magnesium iodide, n-hexyl magnesium bromide, n-hexyl magnesium chloride and n-hexyl magnesium iodide, and the like; alkyllithiums such as methyllithium, ethyllithium, n-propyllithium, isopropyllithium, n-butyllithium, tert-butyllithium, n-pentyllithium, n-hexyllithium and the like; zinc compounds such as methylzinc iodide, ethylzinc iodide, and the like.

Preferred compounds for use as alkylating agent of the formula (5) are those wherein M is a group of the formula: MgX (Grignard reagents). Especially preferred alkylating agents of the formula (5) are methyl magnesium bromide, methyl magnesium chloride and methyl magnesium iodide. The alkylating agents may be used singly or in combination of two or more.

The reaction between the compound of the formula (3) and the alkylating agent of the formula (5) is usually carried out in a suitable solvent. The solvent may be any conventional solvents unless they give any undesirable effect on the reaction. Such solvent includes, for example, aromatic hydrocarbons such as benzene, toluene and xylene; ethers such as diethyl ether, tetrahydrofuran, dioxane, diethylene glycol dimethyl ether and t-butyl methyl ether; aliphatic or alicyclic hydrocarbons such as n-hexane, n-pentane and cyclohexane; and the like; or a mixture thereof.

The proportions of the compound of the formula (3) and the alkylating agent of the formula (5) are not particularly limited. However, the latter is usually used in an amount of at least 1 mole, preferably from 1 to 5 moles, per mole of the former.

The reaction between the compound of the formula (3) and the alkylating agent of the formula (5) may be carried out with cooling or at room temperature or with heating. The reaction is usually carried out at a temperature of from around −30° C. to around 150° C., preferably from around −10° C. to around 70° C., and usually completes in about 1 to about 20 hours.

The fluoro benzoic acid of the formula (2) obtained by the above reaction can easily be isolated by conventional separation methods. Such method includes, for example, extraction with solvents, dilution method, recrystallization, column chromatography and preparative thin-layer chromatography.

According to process A, the alkylating agent of the formula (5) selectively reacts with fluorine at the 2-position of the benzene ring of the compound of the formula (3), thus providing the desired fluoro benzoic acid of the formula (2) in a high yield and high purity.

Secondly, process B is described.

Reaction-2 (Process B)

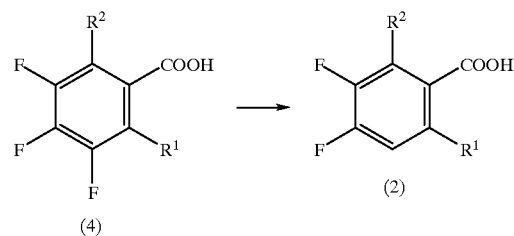

wherein R¹ and R² are as defined above.

In Reaction Scheme-2, the starting compound represented by the formula (4) is a known compound that is easily available.

The compound of the formula (4) includes, for example, 2,3,4,5-tetrafluoro-6-methylbenzoic acid, 2,3,4,5-tetrafluoro-6-ethylbenzoic acid, 2,3,4,5-tetrafluoro-6-n-propylbenzoic acid, 2,3,4,5-tetrafluoro-6-isopropylbenzoic acid, 2,3,4,5-tetrafluoro-6-n-butylbenzoic acid, 2,3,4,5-tetrafluoro-6-tert-butylbenzoic acid, 2,3,4,5-tetrafluoro-6-n-pentylbenzoic acid, 2,3,4,5-tetrafluoro-6-n-hexylbenzoic acid, and the like. Especially preferred is 2,3,4,5-tetrafluoro-6-methylbenzoic acid.

The reaction of converting the compound of the formula (4) into the compound of the formula (2) is carried out by catalytic reduction of the compound of the formula (4) in the presence of a basic compound in a suitable solvent. The solvent may be any conventional solvents unless they give any undesirable effect on the reaction. Such solvent includes, for example, water, acetic acid, alcohols such as methanol, ethanol, isopropanol and polyethylene glycol (PEG); aliphatic or alicyclic hydrocarbons such as n-hexane and cyclohexane; ethers such as dioxane, tetrahydrofuran, diethyl ether and diethylene glycol dimethyl ether; esters such as ethyl acetate and methyl acetate; aprotic polar solvents such as N,N-dimethylformamide (DMF), N-methyl-2-pyrrolidone (NMP), dimethylacetamide (DMA) and hexamethylphosphoric triamide (HMPA); and the like; or a mixture of thereof.

The catalyst for catalytic reduction may be selected from a wide range of known catalysts, such as palladium, palladium-black, palladium-carbon, palladium hydroxide, palladium hydroxide-carbon, rhodium-carbon, platinum, platinum oxide, copper chromite, Raney nickel and the like. The catalytic reduction catalysts may be used singly or in combination of two or more. Of the catalytic reduction catalysts, especially preferred is palladium hydroxide. The amount of the catalyst is not particularly limited but the catalyst is usually used in an amount of from about 0.02 to about 1 times the weight of the compound of the formula (4).

The basic compound may be selected from a wide range of known compounds, for example, inorganic bases such as sodium hydroxide, potassium hydroxide, sodium carbonate, potassium carbonate, sodium hydrogencarbonate, potassium hydrogencarbonate, cesium hydroxide, cesium carbonate, metallic sodium, metallic potassium, metallic magnesium, sodium hydride and sodium amide; metal alcoholates such as sodium methylate, sodium ethylate, potassium t-butoxide, and organic bases such as potassium hexamethyldisilazide. The basic compounds may be used singly or in combination of two or more. The amount of the basic compound is not particularly limited. The basic compound is usually used in an amount of from 1 to 10 moles, preferably from 1 to 5 moles, per mole of the compound of the formula (4).

The catalytic reduction reaction may be carried out with cooling or at room temperature or with heating. The reaction is usually carried out at a temperature of from around −20° C. to around 100° C., preferably from around 0° C. to room temperature at a hydrogen pressure of from 1 to 10 atm. The reaction is usually completed in about 0.5 to about 10 hours.

A reaction accelerator may be added to the catalytic reduction reaction system. Such reaction accelerator includes, for example, crown ethers such as 12-crown-4, 15-crown-5, 18-crown-6 and dibenzo-18-crown-6; polyoxyamines such as tris [2-(2-methoxyethoxy)ethyl]amine; polyamines such as pentaethylenetetramine and pentaethylenehexamine; and the like. The reaction accelerators may be used singly or in combination of two or more.

The fluoro benzoic acid of the formula (2) obtained by the above reduction reaction can easily be isolated by conventional separation methods. Such method includes, for example, extraction with solvents, dilution method, recrystallization, column chromatography and preparative thin-layer chromatography.

The fluoro benzoic acid of the formula (2) prepared according to the process of the present invention can be converted into a benzo heterocyclylic derivative (1) useful as an antibacterial agent, according to the process shown below in Reaction Scheme-3 and in Reaction Scheme-4.

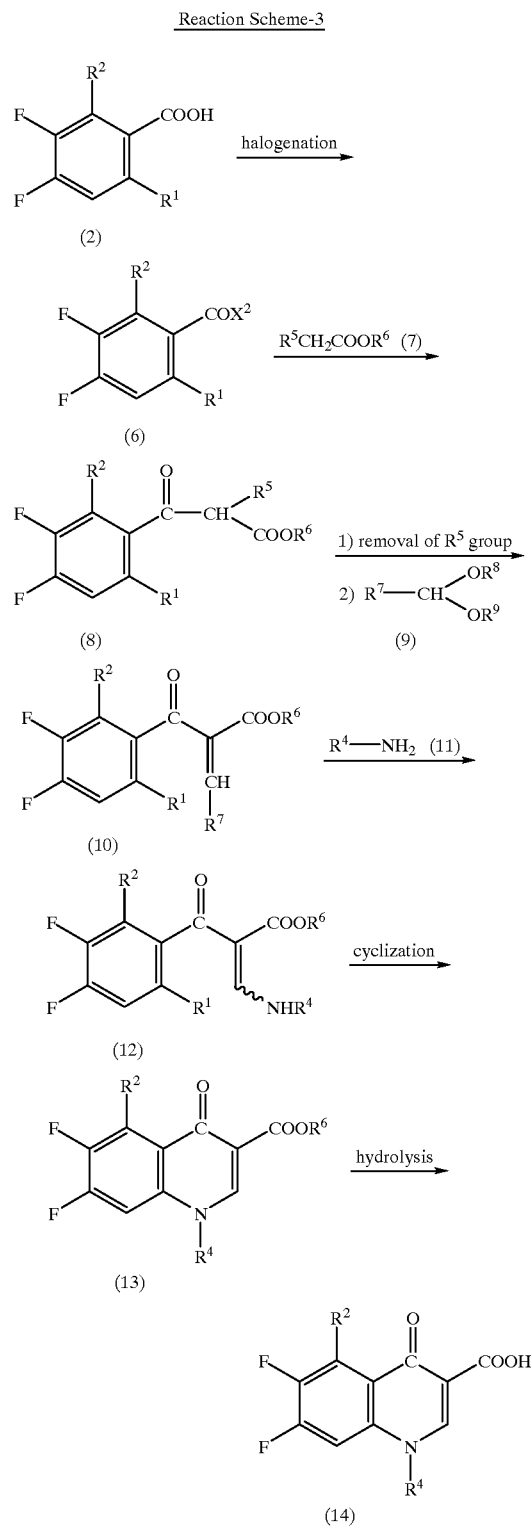

wherein $R^1$, $R^2$ and $R^4$ are as defined above, $R^5$ is a group of the formula: —$COR^{10}$ (wherein $R^{10}$ is $C_{1-6}$ alkyl) or —$COOR^{11}$ (wherein $R^{11}$ is hydrogen, $C_{1-6}$ alkyl or a metal such as sodium, potassium, lithium, 1/2 magnesium or 1/2 zinc), $R^6$ is $C_{1-6}$ alkyl, $R^7$ is a group of the formula: —$NR^{12}R^{13}$ (wherein $R^{12}$ and $R^{13}$ are each $C_{1-6}$ alkyl) or $C_{1-6}$ alkoxy, $X^2$ is halogen, and $R^8$ and $R^9$ are each $C_{1-6}$ alkyl.

The halogenation of the compound of the formula (2) is carried out by reacting the compound of the formula (2) with a halogenating agent in the presence or absence of a solvent. The solvent includes esters such as ethyl acetate and methyl acetate; aromatic hydrocarbons such as benzene, toluene and xylene; halogenated hydrocarbons such as dichloromethane, chloroform and carbon tetrachloride; ethers such as dioxane, tetrahydrofuran and diethyl ether; DMF, dimethylsulfoxide (DMSO); and the like. The halogenating agent may be any conventional halogenating agents which can convert hydroxy in a carboxyl group into a halogen atom. The halogenating agent includes, for example, thionyl chloride, phosphorus oxychloride, phosphorus oxybromide, phosphorus pentachloride, phosphorus pentabromide, and the like. The proportions of the compound (2) and the halogenating agent are not particularly limited and may be suitably selected from a wide range, but, in case of using no solvents, the halogenating agent is usually used in a large excess amount, and in case of using a solvent, the halogenating agent is usually used in an amount of at least 1 mole, preferably 2 to 4 moles per mole of the compound (2). The reaction temperature and reaction period of time are not particularly limited, either, but the reaction is usually carried out at a temperature of from room temperature to around 100° C. for about 30 minutes to about 6 hours.

The reaction between the compound of the formula (6) and the compound of the formula (7) is carried out in the presence of a basic compound in a suitable solvent. The solvent used in the reaction may be any conventional solvents unless they give any undesirable effect on the reaction. The solvent includes, for example, ethers such as diethyl ether, dioxane, tetrahydrofuran, monoglyme and diglyme; alcohols such as methanol, ethanol and isopropanol; aromatic hydrocarbons such as benzene, toluene and xylene; aliphatic or alicyclic hydrocarbons such as n-hexane, n-heptane, cyclohexane and ligroin; amines such as pyridine and N,N-dimethylaniline; halogenated hydrocarbons such as chloroform, dichloromethane and carbon tetrachloride; esters such as ethyl acetate and methyl acetate; aprotic polar solvents such as DMF, DMSO and HMPA; or a mixture of thereof. The basic compounds employed in the reaction includes inorganic bases such as metallic sodium, metallic potassium, metallic magnesium, sodium hydride, sodium amide, sodium hydroxide, potassium hydroxide, sodium carbonate, potassium carbonate, sodium hydrogencarbonate and magnesium chloride; metal alcoholates such as sodium methylate and sodium ethylate, and organic bases such as pyridine, piperidine, quinoline, triethylamine and N,N-dimethylaniline. The basic compounds may be used singly or in combination of two or more. The reaction is usually carried out at a temperature of from around 0° C. to around 150° C., preferably from around 0° C. to around 120° C. The reaction is usually completed in about 0.5 to about 20 hours. The proportions of the compound of the formula (6) and the compound of the formula (7) are such that the latter is usually used in an amount of at least 1 mole, preferably 1 to 2 moles, per mole of the former. The basic compound is usually used in an amount of at least 1 mole, preferably 1 to 2 moles, per mole of the compound of the formula (6).

When the compound of the formula (8) is a compound wherein $R^5$ is the group of the formula: —$COR^{10}$, the reaction for removal of the group: —$COR^{10}$ from the compound is carried out in a suitable solvent in the presence of a basic compound. The solvent used in the reaction includes, for example, ethers such as diethyl ether, dioxane, tetrahydrofuran, monoglyme and diglyme; aromatic hydrocarbons such as benzene, toluene and xylene; aliphatic or alicyclic hydrocarbons such as n-hexane, n-heptane and cyclohexane; aprotic polar solvents such as DMF, DMSO, HMPA, and the like. The basic compound includes ammonia gas, aqueous ammonia, ammonium salts such as ammonium chloride, primary or secondary amines such as ethylamine, diethylamine and piperidine, and the like. The reaction is usually carried out at a temperature of from around 0° C. to around 150° C., preferably from room temperature to around 100° C. The reaction is usually completed in about 1 to about 20 hours.

When the compound of the formula (8) is a compound wherein $R^5$ is a group of the formula: —$COOR^{11}$, the reaction for removal of the group —$COOR^{11}$ from the compound is carried out in an aqueous solution in the presence of an acid catalyst. The acid catalyst used in the reaction includes mineral acids such as hydrochloric acid and sulfuric acid and organic acids such as p-toluene sulfonic acid. The reaction is usually carried out at a temperature of from around 0° C. to around 150° C., preferably from room temperature to around 100° C. The reaction is usually completed in about 1 to about 20 hours.

The reaction between the obtained $R^5$ group-removed compound and the compound of the formula (9) is carried out in a suitable solvent. The solvent employed in the reaction may be any solvents which are used in the above reaction for the removal of the $R^5$ group ($COR^{10}$ group) in addition to anhydrous alkanoic acids such as acetic anhydride, esters such as ethyl acetate and methyl acetate, and the like. The reaction is usually carried out at a temperature of from around 0° C. to around 200° C., preferably from around 0° C. to around 150° C. The reaction is usually completed in about 0.5 to about 10 hours. The compound of the formula (9) is used in an equimolar to large excess amount, preferably in an equimolar to 2-fold molar amount, based on the compound of the formula (8). In case of using a compound of the formula (9) wherein $R^7$ is $C_{1-6}$ alkoxy, the reaction may also be carried out by using acid anhydrides such as acetic anhydride as solvents as well as the above-mentioned solvents. The reaction is usually carried out at a temperature of from around 0° C. to around 200° C., preferably at from around 0° C. to around 170° C.

The reaction between the compound of the formula (10) and the compound of the formula (11) is carried out in a suitable solvent. The solvent employed in the reaction may be any conventional solvents unless they give any undesirable effect on the reaction. The solvent used in the reaction includes, for example, alcohols such as methanol, ethanol and propanol; ethers such as diethyl ether, dioxane, tetrahydrofuran, monoglyme and diglyme; aromatic hydrocarbons such as benzene, toluene and xylene; aliphatic or alicyclic hydrocarbons such as n-hexane, n-heptane, cyclohexane and ligroin; halogenated hydrocarbons such as chloroform, methylene chloride and carbon tetrachloride; and aprotic polar solvents such as acetonitrile, DMF, DMSO, HMPA, NMP and 1,3-dimethyl-2-imidazolidinone (DMI), and the like. The compound of the formula (11) is usually used in an amount of at least 1 mole, preferably 1 to 2 moles, per mole of the compound of the formula (10). The reaction is usually carried out at a temperature of from around −20° C. to around 150° C., preferably from around 0° C. to around 100° C., and usually completed in about 0.1 to about 15 hours. In the reaction, a basic compound may optionally be added to the reaction system. Such basic compound may be any basic compounds which are used for the reaction of converting the compound of the formula (6) to the compound of the formula (7) as shown in Reaction Scheme-3.

The cyclization reaction of the compound of the formula (12) is carried out in a suitable solvent in the presence of a basic compound. The solvent employed in the reaction may be any conventional solvents unless they give any undesirable effect on the reaction. The solvent includes, for example, ethers such as diethyl ether, dioxane, tetrahydrofuran, monoglyme and diglyme; aliphatic or alicyclic hydrocarbons such as n-hexane, n-heptane and ligroin; halogenated hydrocarbons such as chloroform, methylene chloride and carbon tetrachloride; aprotic polar solvents such as acetonitrile, DMF, DMSO, HMPA, NMP and DMI; and the like. The basic compounds employed in the reaction includes inorganic bases such as metallic sodium, metallic potassium, sodium hydride, sodium amide, sodium hydroxide, potassium hydroxide, sodium carbonate and potassium carbonate; metal alcoholates such as sodium methylate and sodium ethylate, organic bases such as 1,8-diazabicyclo[5,4,0]undecene-7 (DBU), N-benzyltrimethylammonium hydroxide and tetrabutylammonium hydroxide; and the like. The basic compound is usually used in an amount of at least 1 mole, preferably 1 to 2 moles, per mole of the compound of the formula (12). The reaction is usually carried out at a temperature of from around 0° C. to around 200° C., preferably from room temperature to around 150° C. The reaction is usually completed in about 0.5 to about 15 hours.

The hydrolysis reaction of the compound of the formula (13) can be carried out under the conditions of conventional hydrolysis, for instance, in the presence of a basic compound in a solvent. The basic compound includes, for example, sodium hydroxide, potassium hydroxide, barium hydroxide or potassium carbonate; a mineral acid such as sulfuric acid, hydrochloric acid or nitric acid; or an organic acid such as acetic acid or aromatic sulphonic acids. The solvent includes, for example, alcohols such as water, methanol, ethanol and isopropanol; ketones such as acetone and methyl ethyl ketone; ethers such as dioxane and ethylene glycol diethyl ether; acetic acid or a mixture of thereof. The reaction is usually carried out at a temperature of from room temperature to around 200° C., preferably from room temperature to around 150° C. The reaction is usually completed in about 0.1 to about 30 hours.

By the reaction, there is produced the compound of the formula (14).

Reaction Scheme-4

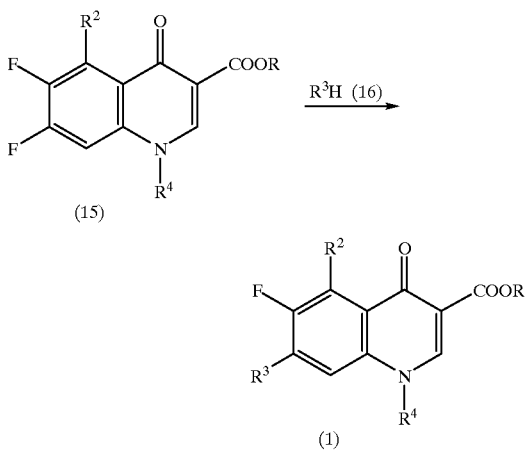

wherein $R^2$, $R^3$, $R^4$ and R are as defined above.

The compound of the formula (15) includes the compound of the formula (13) and the compound of the formula (14) obtained in Reaction Scheme-3.

In the reaction between the compound of the formula (15) and the compound of the formula (16), the proportions of the compounds are not particularly limited and may be selected from a wide range. However, the latter is usually used in an amount of at least 1 mole, preferably about 1 to 5 moles, per mole of the former. The reaction is carried out in an inert solvent. The inert solvent includes, for example, water; alcohols such as methanol, ethanol, isopropanol, butanol, amyl alcohol and isoamyl alcohol; aromatic hydrocarbons sush as benzene, toluene and xylene; ethers such as tetrahydrofuran, dioxane and diglyme; dimethyl acetamide, acetonitrile, DMF, DMSO, HMPA and NMP; and the like; or a mixture thereof. Among these solvents, preferred are acetonitrile, DMF, DMSO, HMPA and NMP. The reaction may also be carried out in the presence of a deacidification agent. The deacidification agent includes, for example, inorganic carbonates such as sodium carbonate, potassium carbonate, sodium hydrogencarbonate and potassium hydrogencarbonate; and organic bases such as pyridine, quinoline and triethylamine. Alkaliine metal halides such as potassium fluoride and lithium chloride and alkaline earth metal halides such as magnesium chloride may also be added to the reaction system. The reaction is usually carried out under a pressure of from 1 to 20 atom, preferably from 1 to 10 atom, at a temperature of from room temperature to around 250° C., preferably from room temperature to around 200° C. The reaction is usually completed in about 10 minutes to about 30 hours.

When the compound of the formula (1) is a compound wherein R is $C_{1-6}$ alkyl, the compound can be hydrolyzed to the corresponding compound of the formula (1) wherein R is hydrogen. The hydrolysis can be carried out under reaction conditions similar to those used for the hydrolysis of the compound (13) shown in Reaction Scheme-3.

The compounds obtained according to the above Reaction Schemes can easily be isolated by conventional separation methods. Such method includes, for example, extraction with solvents, dilution method, recrystallization, column chromatography and preparative thin-layer chromatography.

The single step process according to the present invention produces a fluoro benzoic acid of the formula (2) in high purity and high yield at low costs on a commercial scale by a simple and convenient procedure, without the necessity of undertaking multiple steps, the fluoro benzoic acid being used as an intermediate for preparing a benzo heterocyclic derivative of the formula (1) which is useful as an antibacterial agent.

BEST MODE FOR CARRYING OUT THE INVENTION

The present invention is described below in more detail with reference to Examples and Reference Examples.

Example 1

200 mg of 2,3,4,6-tetrafluorobenzoic acid was dissolved in 10 ml of diethyl ether and cooled to −10° C. in an argon atmosphere. Then 1.72 ml of a methyl magnesium bromide-diethyl ether solution (3 moles/liter) was added dropwise. After completion of dropwise addition, the reaction mixture was heated to room temperature and stirred at room temperature for 17 hours. The reaction mixture was added to about 50 ml of cold water and adjusted to pH 1 with concentrated hydrochloric acid. The reaction mixture was extracted with ethyl acetate and separated into liquids. The organic layer was separated, dried over anhydrous sodium sulfate and concentrated to give 181 mg of 3,4,6-trifluoro-2-methylbenzoic acid (yield: 92%).

Purity: 98%, m.p.: 104.0° C.–105.0° C., white granular crystals.

Example 2

To a solution of 1.04 g of 2,3,4,5-tetrafluoro-6-methylbenzoic acid in 15 ml of ethanol were added 840 mg of potassium hydroxide, 232 mg of pentaethylene hexamine and 200 mg of 20% palladium hydroxide. The mixture was stirred in a hydrogen atmosphere at room temperature for 3 hours. After addition of water, the reaction mixture was filtrated through celite and the filtrate was washed with diethyl ether. The aqueous layer was adjusted to pH 1 with concentrated hydrochloric acid and extracted with dichloromethane. After evaporating the solvent, the residue was purified by silica gel column chromatography (eluent; ethyl acetate:n-hexane=1:3) to give 761 mg of 3,4,6-trifluoro-2-methylbenzoic acid (yield: 80%).

Purity: 98%, m.p.: 104.0° C.–105.0° C., white granular crystals.

Reference Example 1

7 ml of thionyl chloride was added to 3.2 g of 2-methyl-3,4,6-trifluorobenzoic acid, followed by heating and refluxing for 1 hour. The reaction mixture was concentrated, giving 3.3 g of 2-methyl-3,4,6-trifluorobenzoyl chloride. Then 5 ml of toluene was added to the resulting 2-methyl-3,4,6-trifluorobenzoyl chloride to give a toluene solution.

Separately, 0.9 ml of absolute ethanol and two drops of carbon tetrachloride were added to 0.4 g of metallic magnesium. When a reaction began, a mixture of 2.6 ml of diethyl malonate, 1.6 ml of absolute ethanol and 6 ml of toluene was added dropwise to the reaction mixture at a temperature not higher than 60° C., followed by stirring at 60° C. for 1 hour to give ethoxymagnesium ethyl malonate.

To a solution containing ethoxymagnesium ethyl malonate was added dropwise the toluene solution of 2-methyl-3,4,6-trifluorobenzoyl chloride prepared above at a temperature not higher than 0° C. After stirring for 30 minutes, a mixture of 0.4 ml of concentrated sulfuric acid and 6 ml of water was added, followed by extraction with diethyl ether. The extract was dried over magnesium sulfate and concentrated to give 5.2 g of diethyl 2-methyl-3,4,6-trifluorobenzoylmalonate.

Reference Example 2

To 5.1 g of diethyl 2-methyl-3,4,6-trifluorobenzoylmalonate were added 20 ml of water and 30 mg of p-toluenesulfonic acid, followed by heating and refluxing for 2.5 hours. After cooling, the mixture was extracted with diethyl ether. The extract was dried over magnesium sulfate and concentrated to give 3.3 g of ethyl 2-methyl-3,4,6-trifluorobenzoylacetate.

Reference Example 3

To 3.2 g of ethyl 2-methyl-3,4,6-trifluorobenzoylacetate were added 3.0 g of acetic anhydride and 2.7 g of ethyl orthoformate, followed by heating and refluxing for 1 hour. The resulting mixture was concentrated to give 3.5 g of ethyl 2-(2-methyl-3,4,6-trifluorobenzoyl)-3-ethoxyacrylate.

Reference Example 4

3.5 g of ethyl 2-(2-methyl-3,4,6-trifluorobenzoyl)-3-ethoxyacrylate was dissolved in 25 ml of ethanol, and thereto 0.84 ml of cyclopropylamine was added dropwise under ice-cooling. After stirring at room temperature for 30 minutes, the reaction mixture was concentrated. The residue was purified by silica gel column chromatography (eluent; dichloromethane : n-hexane=1:1) to give 2.7 g of ethyl 2-(2-methyl-3,4,6-trifluorobenzoyl)-3-cyclopropylaminoacrylate.

Reference Example 5

2.6 g of ethyl 2-(2-methyl-3,4,6-trifluorobenzoyl)-3-cyclopropylaminoacrylate was dissolved in 26 ml of anhydrous dioxane, and thereto 0.38 g of 60% sodium hydride was added portionwise under ice-cooling. After stirring at room temperature for 30 minutes, the mixture was poured into ice water and extracted with dichloromethane. The extract was dried over magnesium sulfate and concentrated. Diethyl ether was added to the residue and the resulting crystals were filtered, followed by recrystallization from ethanol to give 2.0 g of ethyl 1-cyclopropyl-6,7-difluoro-5-methyl-1,4-dihydro-4-oxoquinoline-3-carboxylate.

m.p.: 185° C.–187° C.

Reference Example 6

20 ml of 90% acetic acid and 5 ml of concentrated hydrochloric acid were added to 1.9 g of ethyl 1-cyclopropyl-6,7-difluoro-5-methyl-1,4-dihydro-4-oxoquinoline-3-carboxylate, followed by refluxing for 2 hours. After cooling, the crystals precipitated were collected by filtration and washed with water, followed by washing with ethanol and then with diethyl ether to give 1.6 g of 1-cyclopropyl-6,7-difluoro-5-methyl-1,4-dihydro-4-oxoquinoline-3-carboxylic acid.

m.p.: 294° C.–298° C., colorless needles $^1$H-NMR (CF$_3$COOD) δ ppm: 1.43–1.55 (2H, m), 1.65–1.81 (2H, m), 3.06 (3H, d, J=2.8 Hz), 4.08–4.20 (1H, m), 8.40 (1H, dd, J=6.8 Hz, 10.3 Hz), 9.46 (1H, s).

Reference Example 7

0.65 g of 2-methylpiperazine was added to a solution of 0.48 g of 1-cyclopropyl-6,7-difluoro-5-methyl-1,4-dihydro-4-oxoquinoline-3-carboxylic acid in 5 ml of N-methyl-2-pyrrolidone, followed by heating at 90° C. for 20 minutes. After distilling off the solvent under reduced pressure, the residue was added with ethanol. The resulting crystals were filtered and recrystallized from ethyl acetate-ethanol to give 231 mg of 1-cyclopropyl-6 -fluoro-7-(3-methyl-1-piperazinyl)-5-methyl-1,4-dihydro-4-oxoquinoline-3-carboxylic acid.

m.p.: 206° C.–208° C., white powder

Reference Example 8

To a suspension of 1.23 g of ethyl 1-cyclopropyl-6,7-difluoro-5-methyl-1,4-dihydro-4-oxoquinoline-3-carboxylate and 254 mg of lithium chloride in acetonitrile was added 1.00 g of 2-methylpiperazine, followed by heating and refluxing for 4 hours. After adding 24 ml of warm water, the reaction mixture was allowed to cool to precipitate crystals and the resulting crystals were filtered and washed with water. The crystals were suspended in 8 ml of isopropyl alcohol and 8 ml of 1N-NaOH, followed by stirring at a temperature in the range of 50° C. to 60° C. for 1 hour. After evaporating the isopropyl alcohol, to the residue were added 40 ml of water and 1.24 ml of concentrated hydrochloric acid, followed by washing with dichloromethane. The aqueous layer was heated at 100° C. for 1 hour to distill off the residual dichloromethane. After the aqueous layer was allowed to cool, 1.04 g of sodium hydrogencarbonate was added and heated with stirring at 60° C. for 1 hour, thereby neutralizing the aqueous layer. The aqueous layer was allowed to cool again, followed by stirring at 0° C. for 1 hour. The resulting crystals were filtered, washed with water and dried at 80° C. for 16 hours to give 1.40 g of 1-cyclopropyl-6-fluoro-7-(3-methyl-1-piperazinyl)-5-methyl-1,4-dihydro-4-oxoquinoline-3-carboxylic acid.

m.p.: 206° C.–208° C., white powder

What is claimed is:

1. A process for preparing a fluoro benzoic acid of the formula (2)

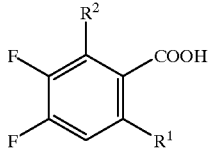

(2)

wherein $R^1$ is halogen and $R^2$ is $C_{1-6}$ alkyl, which comprises alkylating a fluoro benzoic acid of the formula (3)

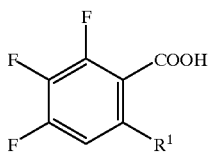

(3)

wherein $R^1$ is as defined above.

2. The process according to claim 1 wherein the alkylating agent used for alkylation is a compound represented by the formula (5)

R²M wherein $R^2$ is as defined above, and M is a group of the formula: —MgX (wherein X is halogen), lithium metal or a group of the formula: ZnX (wherein X is as defined above).

3. The process according to claim 2 wherein the alkylating agent is a compound represented by the formula

R²MgX wherein $R^2$ and X are as defined above.

4. The process according to claim 2 wherein $R^2$ in the formula (5) is methyl.

5. The process according to claim 2 wherein the alkylating agent is used in an amount of at least 1 mole, per mole of the fluoro benzoic acid of the formula (3).

6. The process according to claim 2 wherein the alkylating agent is used in an amount of from 1 to 5 moles, per mole of the fluoro benzoic acid of the formula (3).

7. The process according to claim 1 wherein $R^1$ in the formula (3) is fluorine, chlorine or bromine.

8. The process according to claim 1 wherein $R^1$ in the formula (3) is fluorine or bromine.

9. The process according to claim 1 wherein the reaction temperature is in the range of −30° C. to 150° C.

10. The process according to claim 1 wherein the reaction temperature is in the range of −10° C. to 70° C.

11. A process for preparing a fluoro benzoic acid of the formula (2)

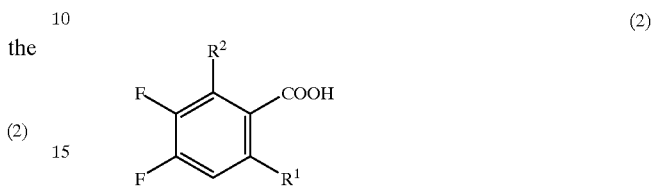

(2)

wherein $R^1$ is halogen and $R^2$ is $C_{1-6}$ alkyl, which comprises reducing a fluoro benzoic acid of the formula (4)

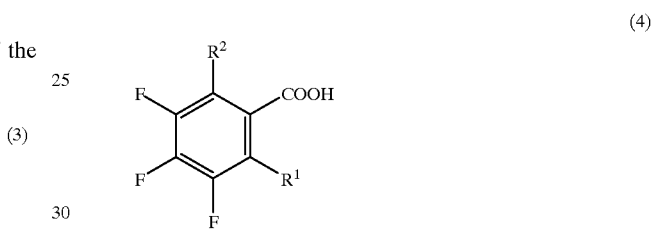

(4)

wherein $R^1$ and $R^2$ are as defined above.

12. The process according to claim 11 wherein the fluoro benzoic acid of the formula (4) is reduced in the presence of a basic compound, using a catalyst for catalytic reduction.

13. The process according to claim 12 wherein the catalyst for catalytic reduction is at least one member selected from the group consisting of palladium, palladium-black, palladium-carbon, palladium hydroxide, palladium hydroxide-carbon, rhodium-carbon, platinum, platinum oxide, copper chromite and Raney nickel.

14. The process according to claim 12 wherein the catalyst for catalytic reduction is palladium hydroxide.

15. The process according to claim 12 wherein the catalyst for catalytic reduction is used in an amount of from 0.02 to 1 times the weight of the fluoro benzoic acid of the formula (4).

16. The process according to claim 11 wherein the catalytic reduction is carried out at a hydrogen pressure of from 1 to 10 atom.

17. The process according to claim 11 wherein the catalytic reduction is carried out at a temperature of from −20° C. to 100° C.

18. The process according to claim 11 wherein the catalytic reduction is carried out at a temperature of from 0° C. to room temperature.

* * * * *